United States Patent [19]

Walsh

[11] Patent Number: 4,911,544
[45] Date of Patent: Mar. 27, 1990

[54] SKIN CONDITION ANALYZER FOR COSMETOLOGISTS

[76] Inventor: John P. Walsh, 344 Appleton St., North Andover, Mass. 01845

[21] Appl. No.: 256,258

[22] Filed: Oct. 6, 1988

Related U.S. Application Data

[63] Continuation of Ser. No. 119,961, Nov. 13, 1987, abandoned.

[51] Int. Cl.$^4$ ............................ G02B 5/10; A61B 5/00
[52] U.S. Cl. .................................... 350/600; 350/601; 362/140
[58] Field of Search ...................... 350/600, 601, 630; 362/135, 140, 144

[56] References Cited

U.S. PATENT DOCUMENTS

| | | | |
|---|---|---|---|
| 2,085,180 | 6/1937 | Bevis | 362/135 |
| 2,779,344 | 1/1957 | Hemmings et al. | 132/83 R |
| 4,241,383 | 12/1980 | Shea | 362/144 |
| 4,380,790 | 4/1983 | Saferstein et al. | 362/140 |

FOREIGN PATENT DOCUMENTS 629081 2/1981 Japan .
59-124501 8/1984 Japan .

OTHER PUBLICATIONS

Meros Chemical Co., Ltd., "Beauty and Health in High Tech Times", Prime Skin Scanner X-1 Technical Brochure (Apr. 1986).
Meros Chemical Co., Ltd., "Beauty and Health in High Tech Times", Prime Skin Scanner Technical Brochure (Apr. 1986).

*Primary Examiner*—Bruce Y. Arnold
*Assistant Examiner*—Martin Lerner
*Attorney, Agent, or Firm*—William Nitkin

[57] ABSTRACT

A device for cosmetic, dermatological and aesthetic analysis of a subject's face for use in beauty salons, cosmetic counters and the like, having a shade with first and second ends, the first end adapted to surround the subject's face, blocking ambient light from the subject's face, a concave mirror disposed at the second end of the shade at a position to magnify the subject's face, the subject's face being viewable by the subject, one or more light sources arrayed within the shade, and means for the operator of the device to view the subject's face while the device is in operation.

6 Claims, 3 Drawing Sheets

SKIN CONDITION ANALYZER FOR COSMETOLOGISTS

This is a continuation of application Ser. No. 119,961 filed Nov. 13, 1987, now abandoned.

BACKGROUND OF THE INVENTION

1. Field of the Invention

The device of this invention resides in the area of the analysis of a person's skin condition and more particularly relates to a device which is designed to allow such person to view the condition of his skin under one or more particular light environments and also to allow the operator of the device to view the skin of that individual at the same time for analysis.

2. Description of the Prior Art

It is well known in the cosmetic field that lights of different wave lengths and sources will cause a person's skin to appear differently. In the medical field long length ultraviolet ray lamps, commonly called Woods lights have been used to analyze skin condition, for example, to visualize flourescent microorganisms, hypopigmented areas or other skin conditions. Infrared photography has also been used to make pictures of superficial veins some of which are not discernible to the naked eye.

SUMMARY OF THE INVENTION

It is an object of this invention to provide an improved analytical device for use by cosmetologists and aestheticians for determination of the condition of a person's skin and hair to help indicate which type of cosmetic material would be best suited for such person. The device further allows the individual whose skin is being analyzed to view his or her own facial area and scalp and see the different colors created on the skin by the light used in the device while at the same time allowing the operator of the device to view that individual's skin in order to suggest proper cosmetic and skin-care products based on the condition of that individual's skin.

Different skin conditions will show different colors when exposed to long-length ultraviolet rays. It should be noted that other ultraviolet lights are used for skin treatment such as for tanning and the like. Such ultraviolet lights are generally of the short wave length type which may have a germicidal effect and which may burn the skin. Middle wave length ultraviolet lights are commonly used in sun lamps for tanning and care must be exercised so that such lights do not shine on the eyes. The long wave lengths of ultraviolet lights, however, are generally considered harmless to the eyes. For example, once such a long wave length ultraviolet light is shone on the skin and the skin appears orange to a coral color, such color would indicate that the skin is oily. If the skin appears a dark purple, poor circulation in that area of the skin would be indicated or that the skin was atrophic. If there are brown spots, it may be that the skin has an uneven pigmentation or has been damaged by the sun while if the skin appears bluish-white under such light, a dry or dehydrated condition would be indicated. A white appearance of the skin shows normal skin. Other lights can be used in the device of this invention such as a wide spectrum fluorescent light to show what the skin would look like under normal lighting conditions, and also for certain situations lamps producing infrared light can be used for infrared photography of the skin to show underlying superficial blood vessel structure as will be discussed below.

In some embodiments of the device means to photograph the subject's face can be incorporated as part of the device. The subject on whom the device is being used also has the ability to see his or her own skin condition which feature is important so that he or she will directly see the areas of the skin that may need particular types of cosmetic treatments such as additional skin oils and the like.

In one embodiment, the device of this invention consists of a casing such as a cone member before which or into which the subject places his or her face which cone member extends to an area containing the lighting means which may produce one or more types of light such as ultraviolet light producing bulbs, regular light bulbs, or lights of other spectrums, such light bulbs being operable separately from one another or in combination if desired. A concave mirror is placed at the end of the cone and is positioned so that when the subject places his face in front of the cone member, it will focus the image of the subject clearly so that the subject can view his face clearly and magnified in the concave mirror around which are disposed the light member(s). Means are also provided for the operator to view the subject's face. It is important that the cone member or other equivalent ambient light shades be utilized to prevent ceiling lights or other lights from obscuring the effect that the ultraviolet light would have on the subject's skin. In another embodiment the lights, mirror and viewing device can be contained in a casing with a curtain disposed around the individual to block out the ambient light.

Means can be provided for the operator of the device to also view the subject while the subject is using the device such as a small peephole or or magnifying lens disposed on one side of the mirror. In some embodiments the concave mirror can be only a semi-silvered, so that it is somewhat transparent from the rear to allow the operator to look through that mirror and see the subject's face to help analyze and map out the areas of the subject's face that may need special cosmetic attention. Other operator viewing means can utilize a small hole in the mirror itself which can be looked through by the operator. There should be an area provided for a camera, such as a Polaroid camera or equivalent-type camera with ultraviolet sensitive film, to be aimed at the subject's face to take photographs of the subject for future records or for the subject's use in analyzing what areas of the skin may be, for example, dry and need cosmetic attention. In addition the camera could use infrared film which would show not otherwise visible superficial veins below the surface of the skin to determine the condition of the skin underlying the surface tissue. Also such camera could use normal film to take pictures under the normal spectrum lights that may be disposed in the casing.

DESCRIPTION OF THE PREFERRED EMBODIMENT(S)

Figure 1:
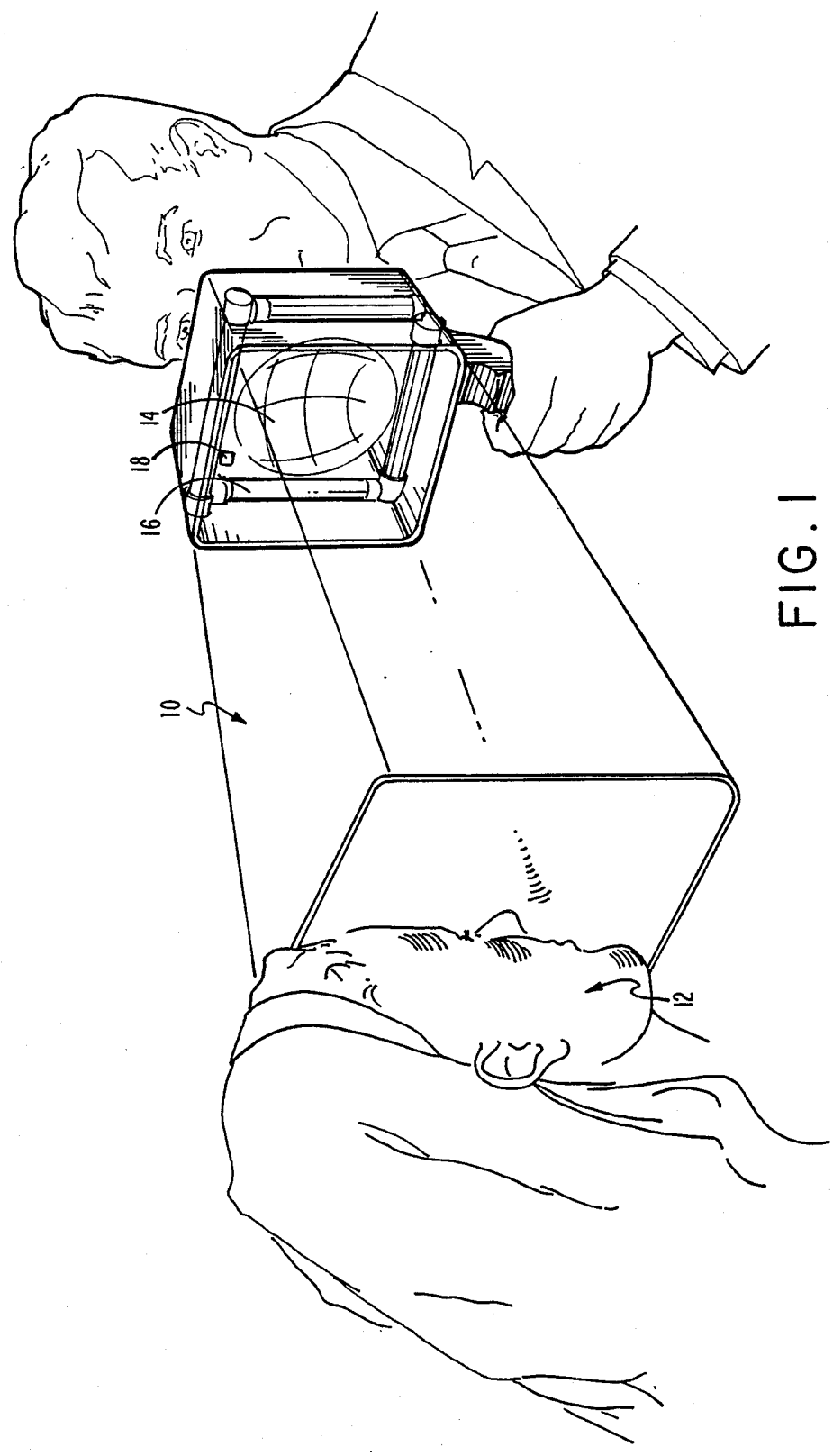
FIG. 1 illustrates a subject using the device of this invention with an operator also viewing the subject's face.
Figure 2:
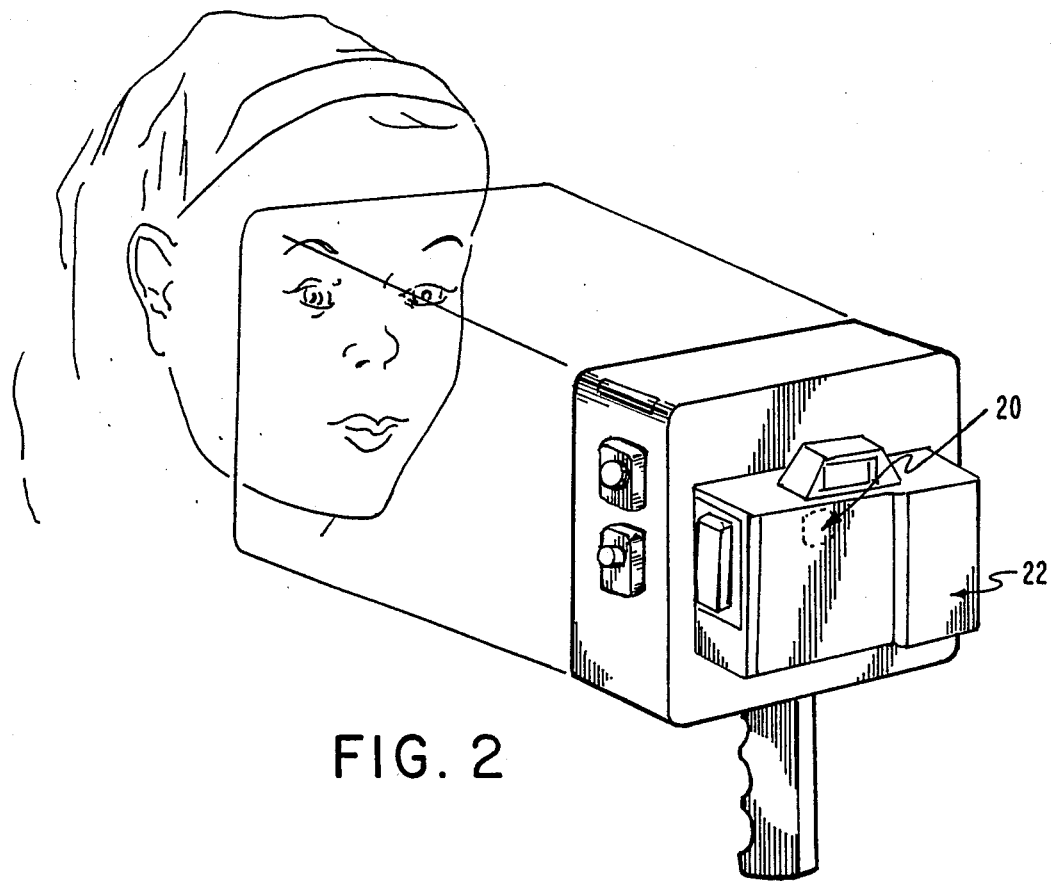
FIG. 2 illustrates the device of this invention with a camera to photograph the subject's face.
Figure 3:
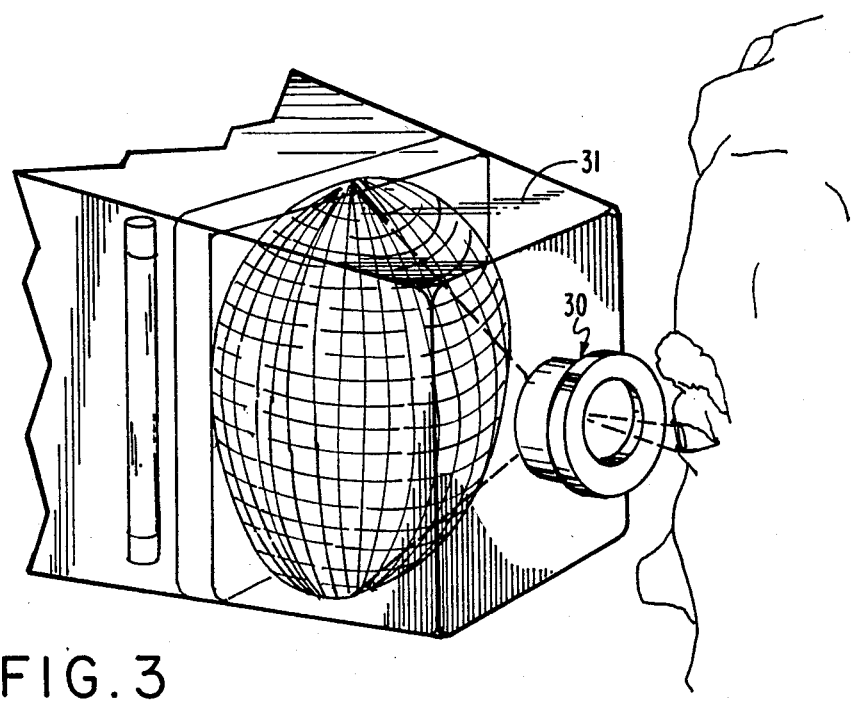
FIG. 3 illustrates a closer view of the device of this invention with a portion of the cone member cut away, such device using a semi-silvered mirror.

In FIG. 1 cone 10 of the device is seen with the subject's face 12 inserted in the open front thereof. Cone member 10 can be of any shape or size, whether conical in configuration or rectangular as long as it comes close to accommodating the perimeter of the subject's face so as to act as a shade to block out extraneous room light therefrom so that only the light from the unit itself will substantially shine on the subject's face. A curtain can extend from the unit cover around the sides and rear of the subject's head to block more ambient light. At the other end of the conical area is concave mirror 14 of the device of this invention which can be a typical cosmetic type which is frequently used to magnify the subject's face. It should be positioned and be of a focal length so that the image of the subject will be focused clearly for the subject to see his or her face magnified although a standard non-magnifying mirror can also be used. Around the mirror disposed away therefrom and in some embodiments having baffles to prevent the light from shining directly on the mirror are light members 16 to provide the type of light desired to be utilized within the device. Some of these light members can be of the long range ultraviolet light producing type and others can be a normal fluorescent or incandescent light source. The lights should be operable either independently or in combination as desired by the operator, such switch means to operate lights independently being well known to anyone skilled in the art of operating light members. At the rear of the unit are means to allow the operator of the unit to view the face of the subject while the device is in operation. Such means can be provided such as by hole 18 defined in one corner where the operator can view the subject's face. In some embodiments a magnifying lens can be placed in hole 18. Also in some embodiments the mirror can be semi-silvered thereby allowing the operator to view the subject's face directly through the mirror from the rear such as illustrated in FIG. 3 or a small hole for viewing can be provided in the mirror such as seen in FIG. 2. Secondary lens 30 seen in FIG. 3 can be positioned in a rear casing 31 of the device for the operator to view the subject through the semi-silvered mirror to allow magnification of the subject's face so that small areas of skin discoloration under a long range ultraviolet light source which might be unobvious from an examination made at a distance can be more easily seen. When using a percentage-silvered mirror, the rear casing prevents light from illuminating the rear of the mirror which would interfere with the operator seeing through the rear of the mirror and also would interfere with the user's reflection if any light were to illuminate the mirror from the rear.

Figure 4:
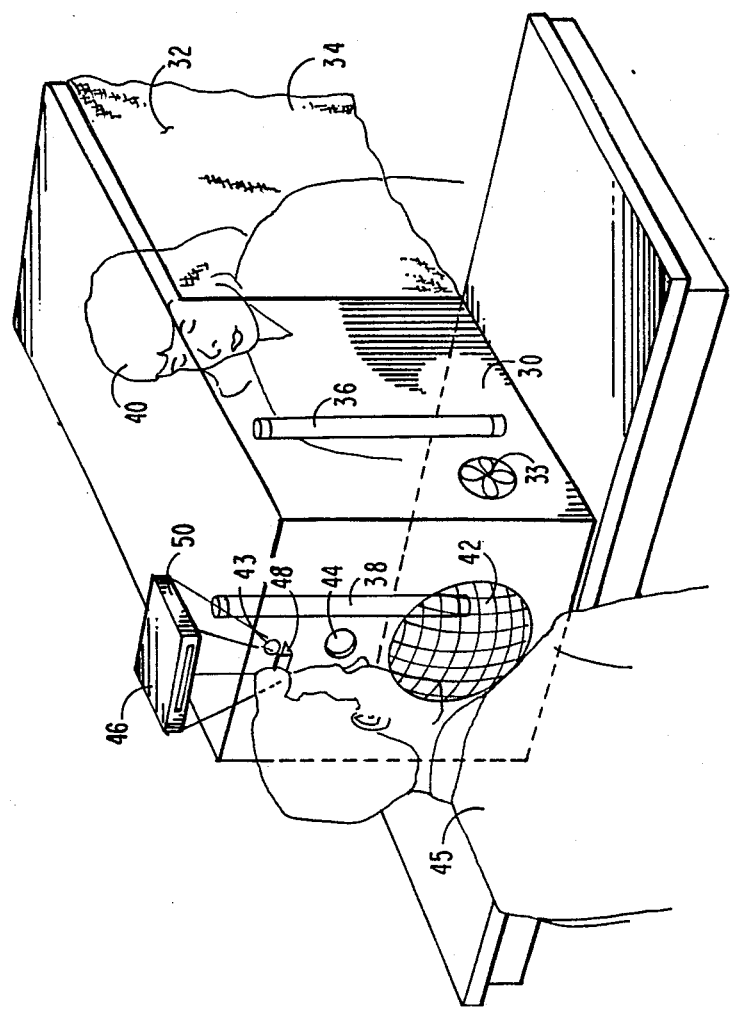
FIG. 4 illustrates a casing in which the user is positioned with a curtain to blockout ambient light.

In some embodiments of the device photographs of the subject under the light source may be desired for future reference and an aperture in the mirror or to the side thereof can be provided for a camera 22 such as a Polaroid camera which is illustrated in FIGS. 2 and 4 to produce instant pictures. The film that is used in the camera can in some embodiments be sensitive to ultraviolet light so that the picture will be substantially the same as what the subject sees. Such aperture can also be provided in the casing of the unit such as through aperture 18 in FIG. 1 or through viewing aperture 20 in the mirror as illustrated in FIG. 2. The entire unit can be placed on a stand and the camera can be attachable with its lens prefocused at the distance of the subject's face and held by retaining members such as quick-release bayonet mounts or equivalent means. Such camera should be of simple operation such as a Polaroid pack film or SX-70 camera or equivalent where once focused on the subject, whether it be fixed-focus or nonfixed-focus such as a focusable single lens reflex, the focus would be on the face and the picture would record the condition of the subject's skin.

FIG. 4 illustrates an alternate embodiment of casing 30 having an opening 32 therein with curtain 34 to block room light. Ultraviolet light members 36 and 38 illuminate the inside of casing 30 and the subject 40 can see her reflection in mirror 42. Operator 45 can also see subject 40 through view hole 44 and camera 46 can be provided to take photographs on ultraviolet-sensitive film or other types of film depending on the type of lights used. A camera attachment aperture 46 can be provided to which the camera is attached. Prism 48 can reflect the image upwards to filmholder 50 to provide a large image which can be focused through lens focused at the plane of the face of subject 40. A fan 33 can be provided to cool and vent the inside of the casing.

Although the present invention has been described with reference to particular embodiments, it will be apparent to those skilled in the art that variations and modifications can be substituted therefor without departing from the principles and spirit of the invention.

I claim:

1. A device used by an operator for cosmetic, dermatological and aesthetic analysis of a subject's face for use in beauty salons, cosmetic counters and the like, comprising:

shade means having first and second ends, said first end adapted to surround the subject's face, blocking ambient light from said face;

a concave mirror disposed at the second end of said shade means at a position to magnify the subject's face, the subject's face being viewable by the subject;

one or more light sources producing light arrayed within said shade means;

means for the operator of said device to view the subject's face while the device is in operation and the subject's face is at the first end of said shade means;

camera means having film sensitive to the light utilized; and means to aim said camera at said subject's face within said shade means.

2. A device used by an operator for cosmetic, dermatological and aesthetic analysis of a subject's face for use in beauty salons, cosmetic counters and the like, comprising:

shade means having first and second ends, said first end adapted to surround the subject's face, blocking ambient light from said face;

a concave mirror disposed at the second end of said shade means at a position to magnify the subject's face, the subject's face being viewable by the subject;

one or more light sources producing light arrayed within said shade means;

means for the operator of said device to view the subject's face while the device is in operation and the subject's face is at the first end of said shade means; and wherein said light source includes a light source producing infrared light and a light source producing long wave ultraviolet light.

3. The device of claim 2 further including camera means having film sensitive to the light utilized and means to aim said camera at said subject's face within said shade means.

4. A device used by an operator for cosmetic, dermatological and aesthetic analysis of a subject's face for use in beauty salons, cosmetic counters and the like, comprising:

a casing having a closed first end and an open second end;

a mirror disposed at the first end of said casing, said second end of said casing adapted to receive said subject;

a curtain attached to said casing and extending around said subject to block ambient light from entering said casing;

one or more light sources disposed in said casing at said first end adapted to shine light on said subject;

means for an operator of said device to view the subject's face while the device is in operation;

wherein said device's light source produces long range ultraviolet light waves;

a camera aperture defined in the first end of said casing; and a camera affixed over said camera aperture to photograph said subject.

5. A device used by an operator for cosmetic, dermatological and aesthetic analysis of a subject's face for use in beauty salons, cosmetic counters and the like, comprising:

shade means having first and second ends, said first end adapted to surround the subject's face, blocking ambient light from said face;

a concave mirror having a front and rear disposed at the second end of said shade means at a position to magnify the subject's face, the subject's face being viewable by the subject from the front of said mirror;

one or more light sources arrayed within said shade means;

means for the operator of said device to view the subject's face while the device is in operation and the subject's face is at the first end of said shade means;

wherein said concave mirror is semi-silvered to allow the operator to view the subject's face directly through said mirror from the rear;

second shade means surrounding the rear of said concave mirror; and an aperture defined in said second shade means through which to view the rear of said concave mirror and the subject's face through said mirror.

6. The device of claim 5 wherein a magnifying lens is positioned in said aperture in said second shade means to magnify the subject's face.

* * * * *